(12) United States Patent
Fukuoka et al.

(10) Patent No.: US 10,709,837 B2
(45) Date of Patent: Jul. 14, 2020

(54) SPIKE CAP AND PRETREATMENT METHOD FOR INFUSION SET USING SAID SPIKE CAP

(71) Applicant: KOBAYASHI & CO., LTD., Taito-ku, Tokyo (JP)

(72) Inventors: Koji Fukuoka, Kobe (JP); Go Kawaoi, Kobe (JP); Kazuyuki Osawa, Kobe (JP); Imari Endo, Kobe (JP)

(73) Assignee: KOBAYASHI & CO., LTD., Tokyo (JP)

( * ) Notice: Subject to any disclaimer, the term of this patent is extended or adjusted under 35 U.S.C. 154(b) by 389 days.

(21) Appl. No.: 15/549,490

(22) PCT Filed: Feb. 9, 2015

(86) PCT No.: PCT/JP2015/053570
§ 371 (c)(1),
(2) Date: Aug. 8, 2017

(87) PCT Pub. No.: WO2016/129047
PCT Pub. Date: Aug. 18, 2016

(65) Prior Publication Data
US 2018/0021511 A1    Jan. 25, 2018

(51) Int. Cl.
*A61M 5/00*    (2006.01)
*A61M 5/162*    (2006.01)
(Continued)

(52) U.S. Cl.
CPC .......... *A61M 5/162* (2013.01); *A61M 5/1407* (2013.01); *A61M 5/158* (2013.01);
(Continued)

(58) Field of Classification Search
CPC .. A61M 5/162; A61M 5/1407; A61M 5/1418; A61M 5/158; A61M 5/1626; A61M 5/165; A61M 5/16827; A61M 39/20; A61M 2005/1402; A61M 2005/1623; A61M 2039/205
See application file for complete search history.

(56) References Cited

FOREIGN PATENT DOCUMENTS

JP    10-108908 A    4/1998
JP    2003-320029 A    11/2003
(Continued)

OTHER PUBLICATIONS

International Search Report dated May 19, 2015, issued in counterpart of International Application No. PCT/JP2015/053570 (2 pages).

*Primary Examiner* — Philip R Wiest
(74) *Attorney, Agent, or Firm* — Westerman, Hattori, Daniels & Adrian, LLP

(57) ABSTRACT

An infusion set employing a spike cap, arranged at which there is an opening configured to prevent passage therethrough of solid or liquid but to allow passage therethrough of gas at interior of the cap, hydrophobic filter being arranged at a location inward from where a tip of spike is inserted at interior of the cap by way of an insertion port, and a lid exterior of the opening for closing the opening; and in which there are hook(s) for anchoring to infusion tubing and a clip equipped with a catch for a flange arranged at the spike. Employing the cap at the infusion set makes it possible to carry out preprocessing including priming and backpriming by a simple operation without leakage of liquid.

8 Claims, 6 Drawing Sheets

(51) Int. Cl.
    *A61M 39/20*     (2006.01)
    *A61M 5/14*     (2006.01)
    *A61M 5/158*     (2006.01)
    *A61M 5/165*     (2006.01)
    *A61M 5/168*     (2006.01)

(52) U.S. Cl.
    CPC .......... *A61M 5/165* (2013.01); *A61M 5/1626* (2013.01); *A61M 5/16827* (2013.01); *A61M 39/20* (2013.01); *A61M 5/1418* (2013.01); *A61M 2005/1402* (2013.01); *A61M 2005/1623* (2013.01); *A61M 2039/205* (2013.01)

(56) References Cited

FOREIGN PATENT DOCUMENTS

| | | |
|---|---|---|
| JP | 2014-217555 A | 11/2014 |
| WO | 2014/021390 A1 | 2/2014 |

SPIKE CAP AND PRETREATMENT METHOD FOR INFUSION SET USING SAID SPIKE CAP

TECHNICAL FIELD

The present invention relates to a spike cap permitting contamination-free priming and backpriming operations to be carried out while making it possible for an infusion container to be pierced on a first attempt, to an infusion set employing said spike cap, and to a pretreatment method comprising priming and backpriming of said infusion set.

BACKGROUND ART

Medical treatments have conventionally been carried out in which therapeutic medications are formulated as infusions which are administered intravenously. Infusions employing therapeutic medications in the form of anticancer agents, nutrients, and the like must typically be administered in high dosages. Furthermore, where a plurality of medications are combined, each infusion must be administered in order, and the total administration dosage is quite high. On the other hand, as administration of infusions continues, because a sudden rise in the concentration of a drug within the blood increases the risk of occurrence of anaphylactic shock, cardiac arrhythmia, and other such side effects, there is a need for physicians and nurses to carefully continue to adjust infusion administration dose while monitoring the condition of the patient. However, carrying out administration by adjusting amount by means of injection is difficult, and as administration time goes on and the number of administrations increases, the patient experiences an increasing amount of bodily pain and is placed under an increasing amount of stress. For this reason, intravenous drip infusion is widely used as a technique for easily and continuously administering infusions to patients intravenously. During intravenous drip infusion, as medical equipment for causing a container having an infusion sealed therewithin to be connected to an intravenous drip needle that has been inserted within a blood vessel of a patient, an infusion set is employed, those in general use conventionally employing soft tubing to link the container having the infusion sealed therewithin with the intravenous drip needle, a mechanism employing a roller clamp and a drip chamber being provided midway along said soft tubing.

Before initiating intravenous drip infusion, physiological saline solution or other such infusion is made to pass through such an infusion set in advance, priming operations being carried out to adequately remove air in advance from the soft tubing, at which time it is necessary to pay adequate attention to ensure that air bubbles originating from such air are not allowed to enter the patient's blood vessel. However, with a conventional infusion set, even where caution is exercised there is a risk that an infusion may leak from the tip of the needle at the downstream-most end of the infusion set during priming, or that an accident could occur in which a hospital room or a hospital wing becomes contaminated, and so there has been a need for a strategy to prevent such accidents.

An infusion set has therefore been proposed that adopts a strategy to reduce the likelihood of leakage of dangerous drugs to the outside environment by splitting the region upstream of the drip chamber into multiple branches to establish two switchable priming flow paths, a shutoff clamp being arranged below the drip chamber and one of the priming flow paths being employed to carry out initial priming, and the priming flow path thereafter being switched, the shutoff clamp below the drip chamber being closed, and the other priming flow path thereafter being used to carry out priming of the remaining priming flow path (see Patent Reference No. 1).

However, while it may be true that the risk of contamination during initial priming is relatively low, the structure of the foregoing proposed infusion set is such that it permits leakage of the dangerous drug from below, and so from the standpoint of whether it adequately prevents leakage of dangerous drugs to the outside environment, there has been a need for further ingenuity. Furthermore, because the structure of the foregoing proposed infusion set is such that terminal portions of the infusion set are open, operations have been complicated inasmuch as there has been a need to exercise care with respect to procedural discharge of physiological saline solution or other such solution used during priming from said terminal portions, and inasmuch as there has been a need for priming, which itself comprises multiple procedural steps, to be carried out twice, and so forth. In addition, with the foregoing proposed infusion set, even where adequate care is exercised with respect to procedural discharge of liquid, there is a risk of occurrence of damage to equipment and/or contamination of the hospital room interior as a result of unintentional spillage of the physiological saline solution that is discharged therefrom onto the infusion set, the stand, the equipment used to carry out intravenous drip infusion, and/or the floor of the hospital room, and so there has been a need for even further ingenuity.

Furthermore, where a plurality of anticancer agents were administered in the form of infusions, it has been necessary to prepare an infusion set in which there are a plurality of sets of secondary tubing arranged therein, and particular attention has also been required to avoid mixture of solutions for which mixture is contraindicated and to see that administration is carried out in the correct order. However, it is often the case that the containers employed for infusions have similar external appearance. For this reason, mixups with respect to the order in which spikes pierce containers, confusion as to which infusion line should be used for different anticancer agent solutions, mistaken order of administration, and other such accidents can easily occur. Efforts have therefore been made to prevent accidents due to human errors by applying labels to the various containers at the time that the infusions are prepared, attaching written warnings, and so forth to clearly specify administration procedure, and to make the various containers recognizable, to establish standard procedures for use specific to each of the various infusion sets with their many different constitutions, to publicize this in advance, and carry out training and so forth, but the situation remains unchanged and misidentification by the operator can still occur, as a result of which there has been a need for improvement.

PRIOR ART REFERENCES

Patent References

Patent Reference No. 1: International Patent Application Publication No. 2014/021390

SUMMARY OF INVENTION

Problem to be Solved by Invention

A problem to be solved by the present invention is to provide a novel spike cap, infusion set employing same, and preprocessing method comprising priming and backpriming of said infusion set, that make it possible to, by means of a simpler procedure, easily, conveniently, and definitively implement the priming and backpriming operations that are carried out prior to use of the infusion set, and in which the risk of occurrence of damage to equipment and contamination of the hospital room interior due to unintentional leakage of liquid from the infusion set while priming and backpriming operations are being carried out or after priming and backpriming operations have been carried out is drastically reduced. Furthermore, a problem to be solved by the present invention is to make it possible to prevent error in the order in which infusions are to be administered, confusion as to which infusions contain different drugs among multiple pieces of infusion tubing, and other accidents that may occur due to the human error of mixing up the order of use of a plurality of spikes provided at an infusion set, and to moreover make it possible to easily establish standard procedures for use.

Means for Solving Problem

A first means in accordance with the present invention for solving the foregoing problems is a spike cap characterized in that arranged thereat is an opening configured so as to not allow passage therethrough of solid or liquid but so as to allow passage therethrough of gas at the interior of the cap, a hydrophobic filter being arranged at a location inward from where the tip of a spike is inserted at the interior of the cap by way of an insertion port for the spike, and a lid for closing said opening at the exterior of said opening.

A second means in accordance with the present invention for solving the foregoing problems is the spike cap according to the first means in accordance with the present invention characterized in that arranged at the exterior of the insertion port for the aforesaid spike is a lid for closing said insertion port.

A third means in accordance with the present invention for solving the foregoing problems is the spike cap according to the first or second means in accordance with the present invention characterized in that the aforesaid spike cap has a clip equipped with a catch for a flange disposed on the spike.

A fourth means in accordance with the present invention for solving the foregoing problems is the spike cap according to any one of the first through the third means in accordance with the present invention characterized in that the aforesaid spike cap has a hook for anchoring to infusion tubing.

A fifth means in accordance with the present invention for solving the foregoing problems is the spike cap according to any one of the first through fourth means in accordance with the present invention characterized in that the hook has a C-shaped configuration, an O-shaped configuration, or a U-shaped configuration.

A sixth means in accordance with the present invention for solving the foregoing problems is the spike cap according to the fourth means or the fifth means in accordance with the present invention characterized in that the aforesaid hook is arranged on said cap so as to cause the insertion port for the spike to be inclined upward or so as to cause said cap to be horizontal when the aforesaid cap is anchored to infusion tubing connected to the spike which is provided at an upstream-most location of a primary tubing branch.

A seventh means in accordance with the present invention for solving the foregoing problems is an infusion set characterized in that the spike cap according to any one of the first through the sixth means in accordance with the present invention is installed on a spike connected to the other end of infusion tubing linked to a secondary tubing branch connector at a three-way stopcock or splitter at the infusion set, and installed at a connector for connection with an intravenous drip needle provided at a downstream-most location of a primary tubing branch in said infusion set is a cap which is for a connector for connection with an intravenous drip needle and arranged at which there is an opening configured so as to not allow passage therethrough of solid or liquid but so as to allow passage therethrough of gas at the interior of the cap, a hydrophobic filter being arranged at a location inward from where the tip of the connector for connection with an intravenous drip needle is inserted at the interior of the cap by way of the insertion port for the connector for connection with an intravenous drip needle, and a lid for closing said opening at the exterior of said opening.

An eighth means in accordance with the present invention for solving the foregoing problems is a preprocessing method comprising priming and backpriming of the infusion set according to the seventh means in accordance with the present invention, the preprocessing method comprising priming and backpriming of said infusion set being characterized in that as a result of a single operation in which the spike disposed at the upstream-most location of the primary tubing branch in the aforesaid infusion set, at which the lids arranged at the opening for the cap for the connector for connection with the intravenous drip needle and the spike cap, infusion set shutoff clamps, levers of three-way stopcocks, and a roller clamp are all placed in their open states, is made to pierce a rubber seal of an infusion container having physiological saline solution sealed therewithin, the physiological saline solution is made to enter an internal cavity of the infusion set, causing air at the interior of the infusion set to be displaced and to be exhausted by way of the hydrophobic filters arranged at the spike cap and cap for the connector for connection with the intravenous drip needle, and causing the internal cavity to be filled with the physiological saline solution, as a result of which priming and backpriming are completes.

BENEFIT OF THE INVENTION

The spike cap of the present invention, when employed in an infusion set, makes it possible to obtain the benefit whereby infusion set priming and backpriming operations are completed in extremely rapid and simple fashion by causing air within the infusion set to be quickly discharged therefrom not only at primary tubing branch(es) but also at secondary tubing branch(es), and simultaneously causing same to be filled with physiological saline solution, as a result of only a single operation in which a spike at an upstream-most location in said infusion set is inserted in an infusion container having sealed therewithin physiological saline solution which is suspended from an IV stand.

In addition, no physiological saline solution whatsoever is discharged from spike cap(s) in accordance with the present invention, and so damage to equipment and contamination do not occur. Moreover, by causing said cap(s) to be provided with clip(s) equipped with catch(es) for flange(s) arranged at spike(s), the cap(s) will not become disengaged even if infusion container(s) is/are pressed on with the hand(s) during priming and backpriming operations. Furthermore, because lid(s) provided on cap(s) are closed following priming and backpriming, physiological saline solution at regions peripheral to hydrophobic filter(s) at cap interior(s) does not spill out from cap insertion port(s). For this reason, because the amount of physiological saline solution that is used can be kept to a minimum, such that an adequate remaining amount is retained therewithin, this permits effective use thereof, as there may be no need to replace infusion container(s) at the time of any medical treatment that may take place thereafter.

Moreover, by causing spike cap(s) in accordance with the present invention to have C-shaped, U-shaped, and/or O-shaped hook(s) for anchoring same to infusion tubing, and causing said hook(s) to be anchored to infusion tubing at set(s) of primary tubing, because it will be possible to cause the center of gravity of the infusion set to shift toward tubing at primary tubing, making it possible to increase the stability of IV stand(s) during priming and backpriming and/or during administration of infusion(s), no abnormal force will act on intravenous drip needle(s), the risk of occurrence of accidents in which intravenous drip needle(s) become detached or there is leakage of liquid will be greatly reduced.

In addition, because employment of the spike cap of the present invention makes it possible to cause anchoring to infusion tubing at set(s) of primary tubing to be done in associated fashion with respect to an order of administration of infusions and/or a procedure for using the infusion set, identification of sets of secondary tubing is facilitated, making it possible to obtain the benefit whereby smooth progress can be made in standardization of operational procedures for use of the infusion set, and medical accidents such as mistaken administration or the like occurring as a result of misidentification by a pharmacist, physician, or nurse, or other such human error, can be prevented.

EMBODIMENTS FOR CARRYING OUT THE INVENTION

Below, embodiments for carrying out the present invention are described as appropriate with reference to the drawings.

Figure 1:
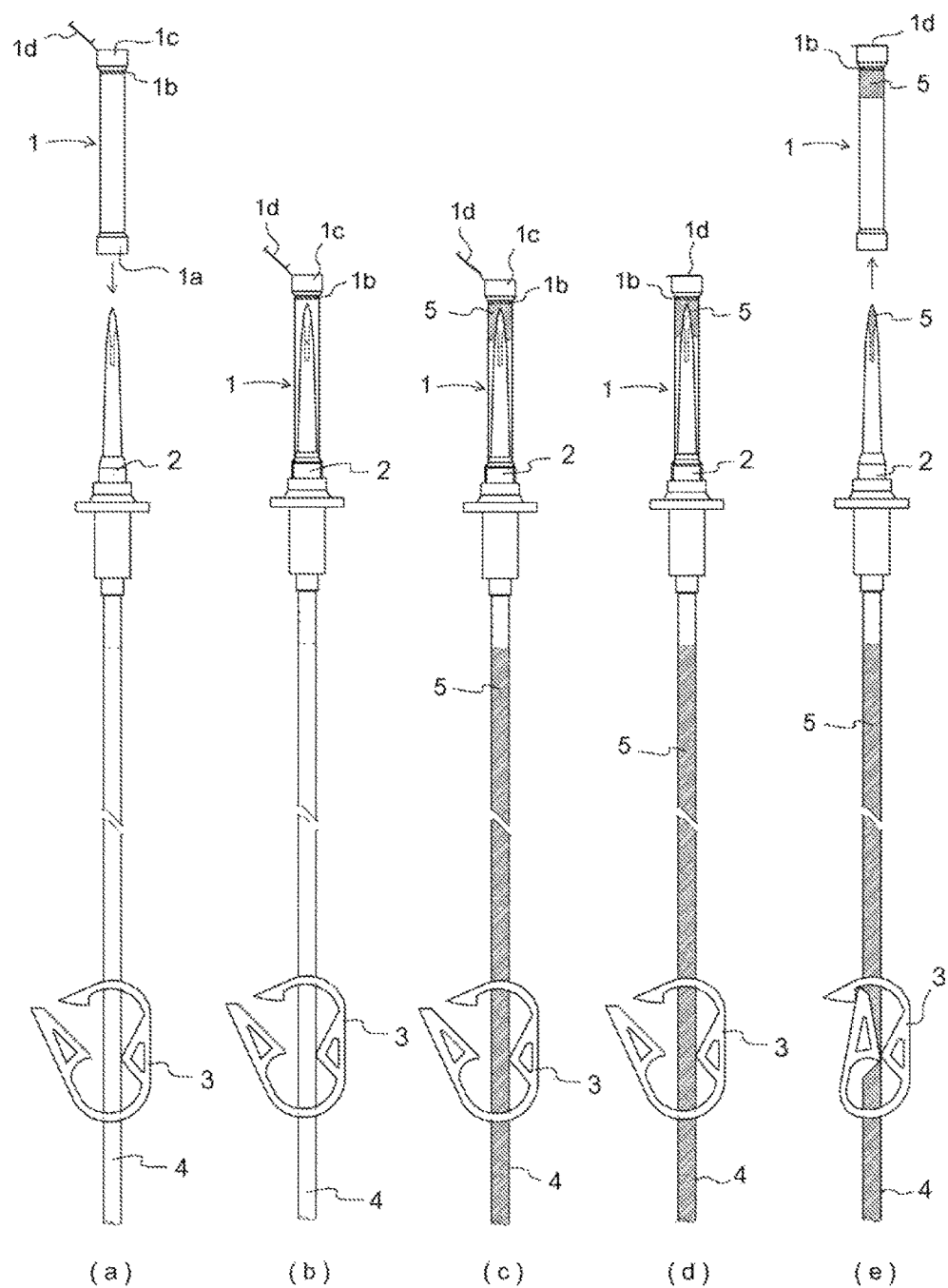
FIG. 1 Drawing for explaining the constitution of a spike cap in accordance with the present invention and a procedure for using said spike cap to carry out preprocessing comprising backpriming of an infusion set. (a) is a drawing for explaining a situation that may exist before spike cap 1 is installed on spike 2. (b) is a drawing for explaining a situation that may exist when cap 1 for installation on a spike is installed on spike 2. (c) is a drawing for explaining a situation that may exist when backpriming is initiated, at which time physiological saline solution 5 enters infusion tubing 4, spike 2, and the interior of spike cap 6. (d) is a drawing for explaining a situation that may exist when lid 1d at said cap is shut after backpriming has been completed. (e) is a drawing for explaining a method employed when cap 1, the lid 1d at which is shut, is removed from spike 2 after backpriming has been completed.

Configuration and Constitution of Spike Cap, and of Infusion Set in which Said Spike Cap is Installed, in Accordance with Present Invention Spike cap 1 in accordance with the present invention has a constitution such that arranged thereat is an opening 1c configured so as to not allow passage therethrough of solid or liquid but so as to allow passage therethrough of gas at the interior of the cap, a hydrophobic filter 1b being arranged at a location inward from where the tip of the spike is inserted at the interior of the cap by way of an insertion port 1a for the spike, and a lid 1d at the exterior of said opening for closing said opening (FIG. 1).

Figure 2:
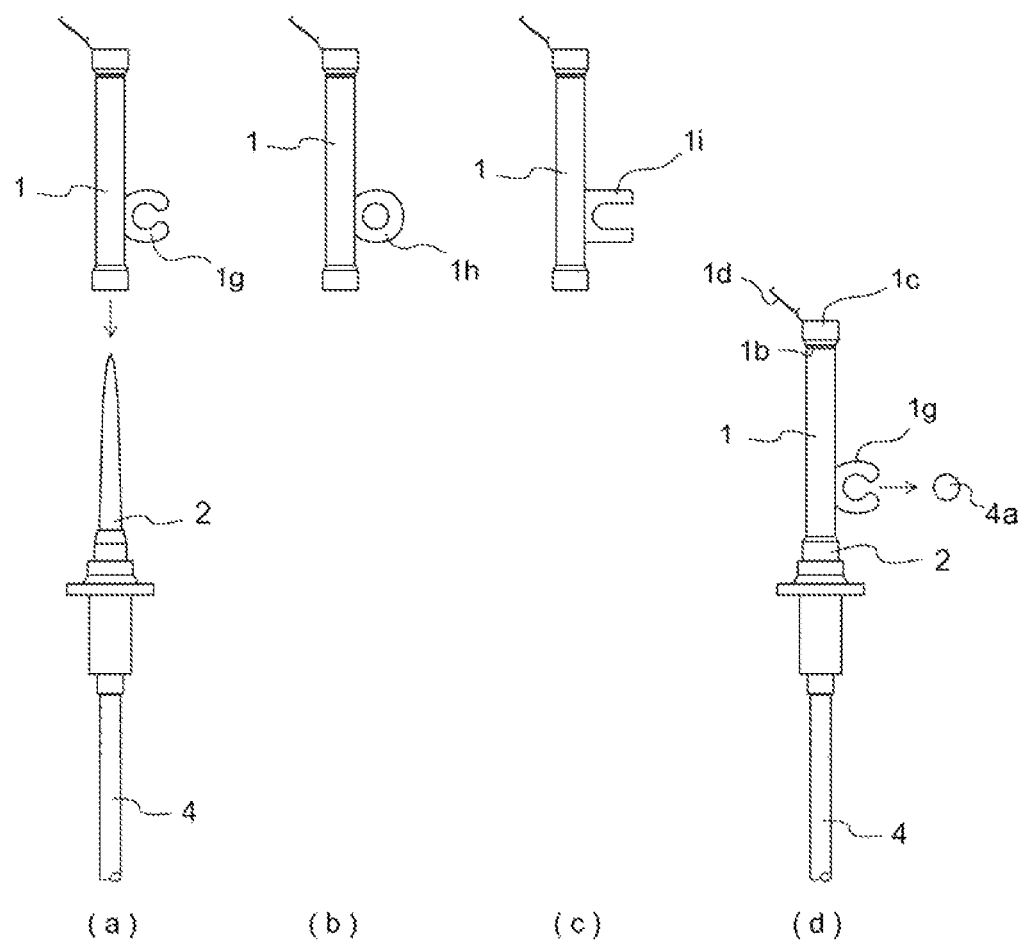
FIG. 2 Drawing for explaining the constitution of spike cap 1, which has a hook in accordance with the present invention, and a method for causing said cap to be installed on a spike 2, and for then causing this to be secured to infusion tubing 4. (a) is a drawing for explaining a situation that may exist before a spike cap which has C-shaped hook 1g is installed on the spike. (b) is a drawing for describing a spike cap which has O-shaped hook 1h. (c) is a drawing for describing a spike cap which has a U-shaped hook 1i. (d) is a drawing for explaining a procedure for causing a cap which has C-shaped hook 1g and which has been installed on spike 2 to thereafter be secured to infusion tubing.

Spike cap 1 in accordance with the present invention may have hook(s) for anchoring said cap to infusion tubing. Said hook(s) may preferably be hook(s) 1g of C-shaped configuration, hook(s) 1h of O-shaped configuration, and/or hook(s) 1i of U-shaped configuration ((a) at FIG. 2, (b) at FIG. 2, and (c) at FIG. 3). In addition, at an infusion set employing spike cap(s) 1 in accordance with the present invention, it is preferred that spike cap(s) 1 having hook(s) disposed on spike(s) 2 at secondary tubing branch(es) be anchored to infusion tubing 4 connected to spike(s) provided at upstream-most location(s) of the infusion set by virtue of the aforesaid hook(s), and where there are a plurality thereof it is desirable that these be anchored in order of use from top to bottom (FIG. 4).

Moreover, it is preferred that the aforesaid hook(s) be arranged on spike cap(s) 1 so as to cause insertion port(s) for spike(s) to be inclined upward and/or so as to cause said cap(s) to be horizontal when the aforesaid cap(s) is/are anchored to infusion tubing connected to spike(s) provided at upstream-most location(s) of primary tubing branch(es). By arranging hook(s) thereon in this way, it is possible to cause the aforesaid cap(s) to be anchored to infusion tubing connected to spike(s) provided at upstream-most location(s) of primary tubing branch(es) in such fashion that insertion port(s) for spike(s) is/are inclined upward and/or the aforesaid cap(s) is/are horizontal, so that even if spike(s) 2 is/are detached therefrom after lid(s) 1d at spike cap(s) 1 is/are closed following pretreatment comprising priming and backpriming of the infusion set, physiological saline solution 5 does not spill out from insertion port(s) 1a at spike cap(s) 1 but is definitively retained at cap interior(s).

Figure 3:
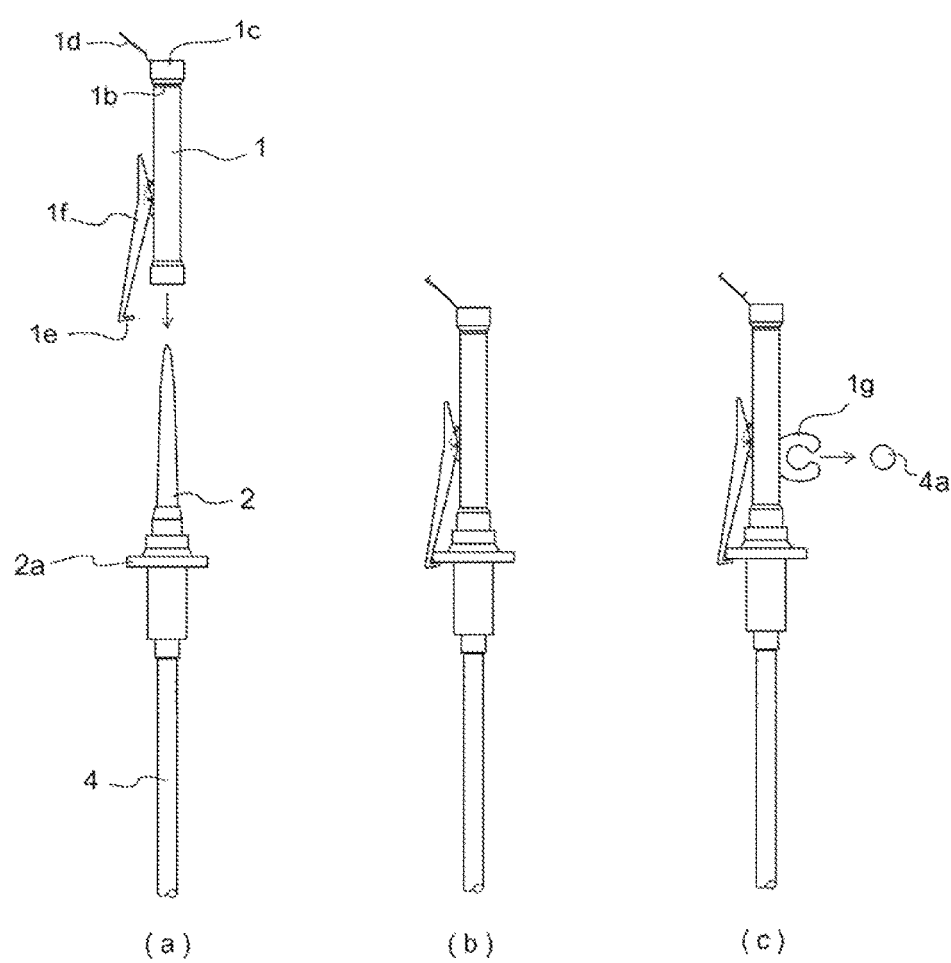
FIG. 3 Drawing for explaining the structure of spike cap 1 having clip 1f equipped with catch 1e for flange 2a arranged at spike 2 in accordance with the present invention, and a method for causing said spike cap to be installed on spike 2. (a) is a drawing for explaining a situation that may exist before the aforesaid spike cap is installed on the spike. (b) is a drawing for explaining a situation that may exist after said cap is installed on the spike. (c) is a drawing for explaining a situation that may exist when the aforesaid spike cap further has C-shaped hook 1g.
Figure 4:
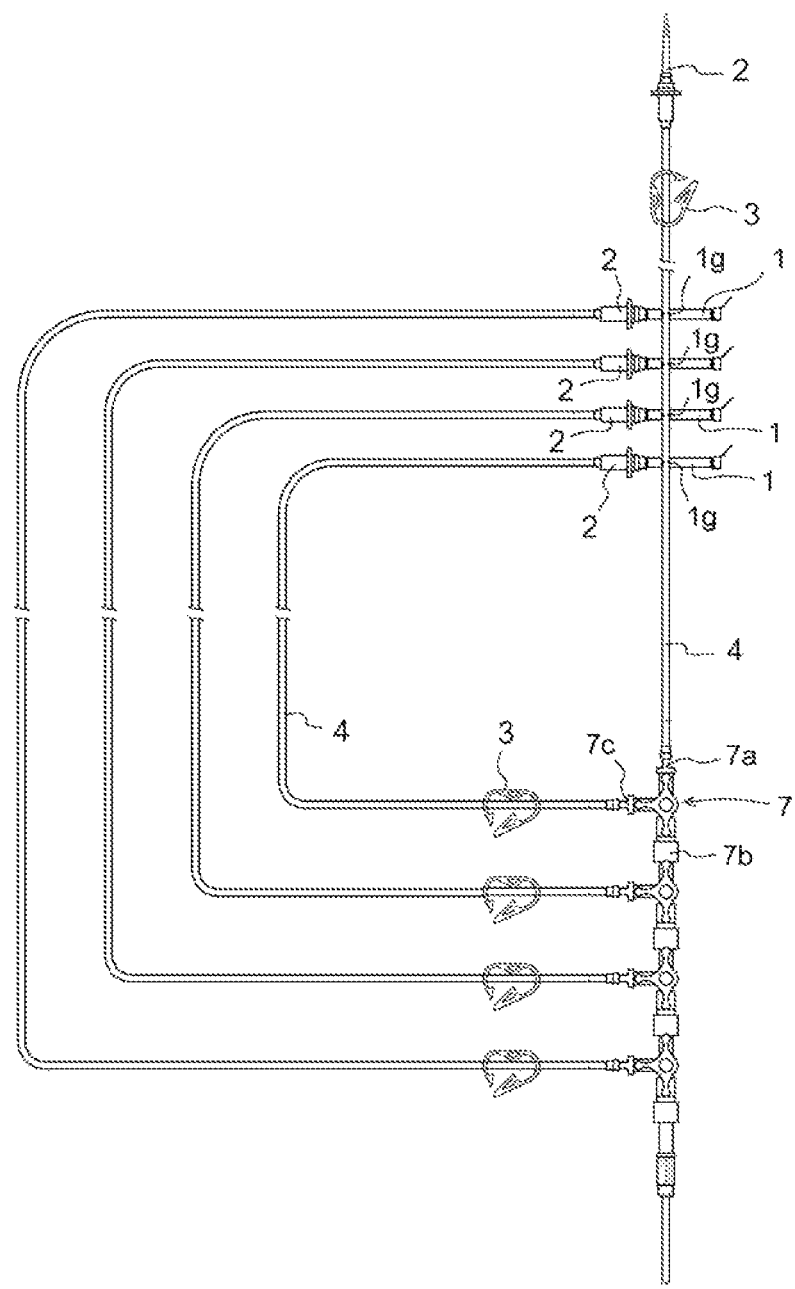
FIG. 4 Drawing for explaining standardization of operational procedures, in which spike caps 6 having hooks in accordance with the present invention are respectively installed on spikes 2 at a plurality of sets of secondary tubing provided at an infusion set, being respectively anchored in horizontal fashion to infusion tubing 4 at the sets of secondary tubing so that the spikes are stacked in order of use starting from the top.

Furthermore, spike cap(s) 1 in accordance with the present invention may have clip(s) 1f equipped with catch(es) for flange(s) 2a provided on spike(s) 2 ((a) at FIG. 3). When spike cap 1 having the aforesaid clip 1f is installed on spike 2, the catch at clip 1f definitively catches onto flange 2a ((b) at FIG. 3). For this reason, even if pressure from physiological saline solution and/or air within infusion tubing such as may result from this being pressed on during backpriming should act thereupon, because spike cap 1 which has clip 1f in accordance with the present invention does not become detached from spike 2 but is able to remain in its installed state, there is no occurrence of accidents such as those in which physiological saline solution used for backpriming leaks out therefrom.

Spike cap 1 which has clip 1f in accordance with the present invention may further have hook(s) for anchoring said cap to infusion tubing. Said hook(s) may preferably be hook(s) 1g of C-shaped configuration, hook(s) 1h of O-shaped configuration, and/or hook(s) 1i of U-shaped configuration ((c) at FIG. 3). As a result of provision of such hook(s), when spike cap 1 having clip 1f in accordance with the present invention is anchored to infusion tubing connected to the spike provided at the upstream-most location of the primary tubing branch, it is possible to cause the insertion port for the spike to be inclined upward and/or said cap to be horizontal, such that there is no occurrence of accidents in which physiological saline solution 5 used for priming and backpriming leak out therefrom.

Figure 5:
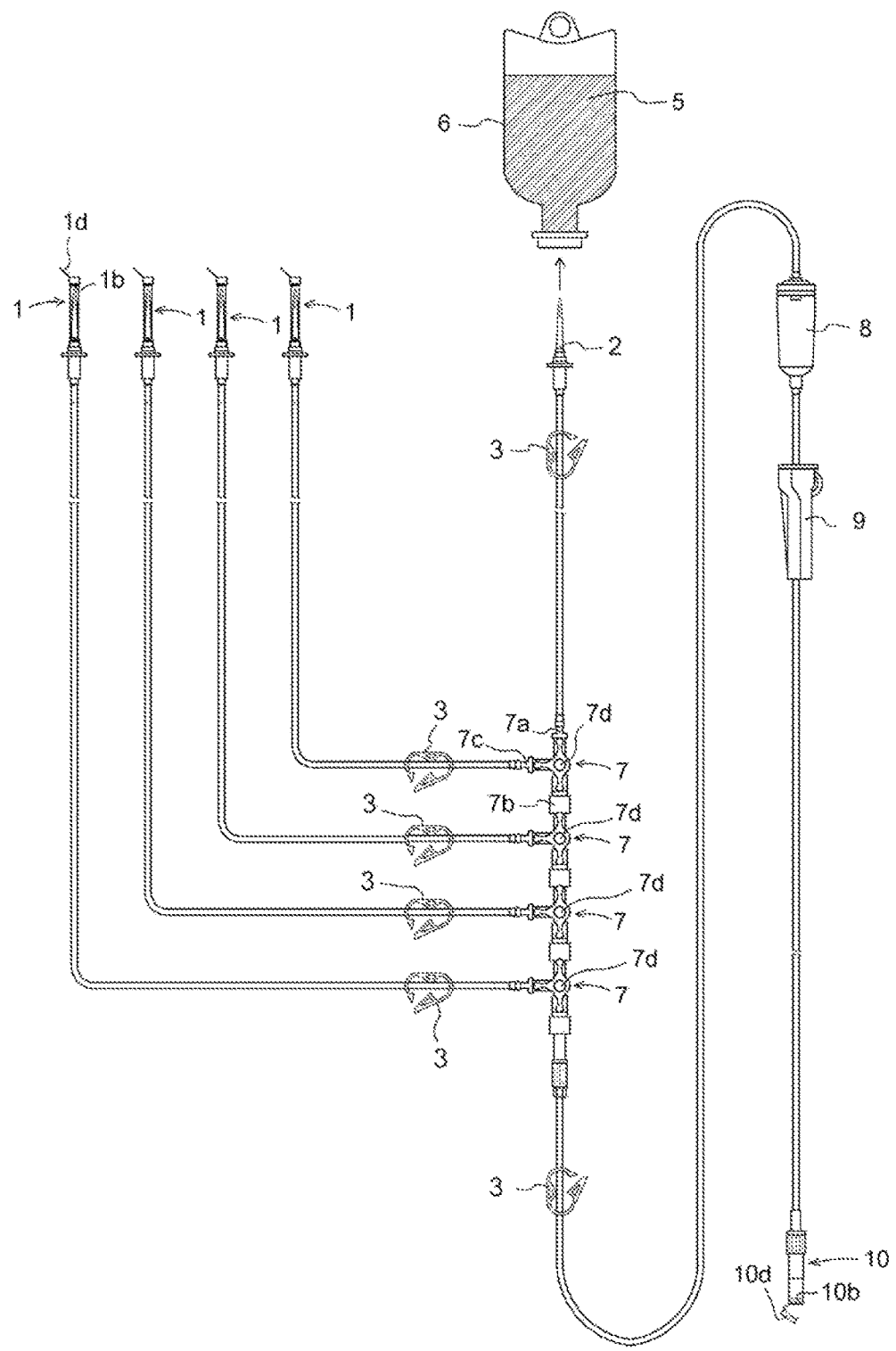
FIG. 5 Drawing for explaining a preprocessing method comprising priming and backpriming in the context of an infusion set employing spike caps 1 in accordance with the present invention.

At an infusion set employing spike cap 1 in accordance with the present invention, respective members are connected so as to have constitution(s) as indicated below. That is, an infusion set in accordance with the present invention has members in the form of the aforesaid spike cap(s) 1; spike(s) 2; shutoff clamp(s) 3 for pressing on and opening and/or closing flow path(s) within infusion tubing; infusion tubing 4; three-way stopcock(s) 7; male connector(s); drip chamber(s) 8; roller clamp(s) 9; connector(s) for connection with intravenous drip needle(s); and cap(s) 10 for connector(s) for connection with intravenous drip needle(s), arranged at which there is/are opening(s) 10c configured so as to not allow passage therethrough of solid(s) or liquid(s) but so as to allow passage therethrough of gas(es) at interior(s) of cap(s), hydrophobic filter(s) 10b being arranged at location(s) inward from where tip(s) of connector(s) for connection with intravenous drip needle(s) is/are inserted at interior(s) of cap(s) by way of insertion port(s) 10a for connector(s) for connection with intravenous drip needle(s); and lid(s) 10d at exterior(s) of said opening(s) for closing said opening(s) (FIG. 5).

In addition, spike(s) 2 is/are provided at upstream-most location(s) of the liquid set, said spike(s) being connected to one end of infusion tubing 4 equipped with shutoff clamp(s) 3 for pressing on and opening and/or closing flow path(s) within infusion tubing, the other end of said infusion tubing 4 being connected to primary tubing upstream branch connector(s) 7a of three-way stopcock(s) 7. In addition, connected to secondary tubing branch connector(s) 7c of three-way stopcock(s) 7 there is/are one end of infusion tubing 4 equipped with shutoff clamp(s) 3 for pressing on and opening and/or closing flow path(s) within infusion tubing, and spike(s) 2 covered with spike cap(s) 1 in accordance with the present invention at the other end of said infusion tubing 4. Furthermore, further connected to primary tubing downstream branch connector(s) 7b of said three-way stopcock(s) 7 there is/are optionally one or more three-way stopcock(s) 7 connected to one end of infusion tubing 4 equipped with shutoff clamp(s) 3 for pressing on and opening and/or closing flow path(s) within infusion tubing connected to spike(s) 2 covered with cap(s) 1 for installation on the aforesaid spike(s) at secondary tubing branch connector(s) 7c. In addition, male connector(s) is/are connected to primary tubing downstream branch connector(s) 7b of the aforesaid three-way stopcock(s) 7 disposed at downstream location(s), one end of infusion tubing 4 equipped with shutoff clamp(s) 3 for pressing on and opening and/or closing flow path(s) within infusion tubing being further connected thereto, drip chamber(s) 8 being connected to the other end of said infusion tubing 4. In addition, this has a constitution such that said drip chamber(s) 8 is/are connected to one end of infusion tubing 4 on which roller clamp(s) 9 is/are installed, the other end of said infusion tubing 4 being connected to connector(s) for connection with intravenous drip needle(s) covered with cap(s) 10 for connection with intravenous drip needle(s). The respective members are in addition connected in advance in the form of a single integral unit which is provided as an infusion set capable of instant use (FIG. 5).

Materials

There is no particular limitation with regard to the materials that may be employed for formation of the members that make up the infusion set of the present invention, it being possible to use materials such as are ordinarily employed in the context of members for infusion sets and medical equipment; for example, Nylon, polycarbonate, polypropylene, polystyrene, and/or other such resin materials and/or stainless steel and/or other such metals may be employed, it being possible to employ polyolefinic resins and/or other such materials suitable for soft tubing at the infusion tubing. Because, depending on the type of drug, e.g., anticancer agent, used, polyethylene terephthalate (PEHP) serving as plasticizer may leach from polyvinyl chloride (PVC), resin materials employed for formation of the members that make up the infusion set of the present invention do not employ polyvinyl chloride, it being preferred that these employ Nylon and/or polycarbonate. Hydrophobic filter(s) may employ polytetrafluoroethylene (PTFE), polyethylene (PE), polyolefin, polypropylene, polyethylene, polyvinylidene fluoride (PVDF), nitrocellulose, and/or the like, it being preferred that polyethylene (PE) and/or polytetrafluoroethylene (PTFE) be employed therefor. Any of the various foregoing resin materials may be employed in colored form. Furthermore, stainless steel and/or other metals may be employed in a form in which the surface thereof has undergone coloration treatment, in which case it is preferred that material(s) which have undergone coloration treatment that is highly anticorrosive be employed.

Manufacturing Operations

The infusion set of the present invention is manufactured in such fashion that the respective members are definitively connected so as to form an infusion set in the form of a single integral unit. There is no particular limitation with regard to the method for definitively connecting the respective members, it being possible to use methods such as are ordinarily employed as methods for obtaining an infusion set or medical equipment in the form of a single integral unit; for example, adhesive operations employing adhesives ordinarily used for infusion sets or other such medical equipment, fusing operations that make use of heat, ultrasonic waves, or the like, and/or other such techniques may be utilized. By providing the infusion set in the form of a single integral unit, the risk that joined parts will become separated is eliminated, making it possible to more definitively prevent medical accidents such as damage to equipment and/or contamination of the hospital room interior due to occurrence of unintentional leakage of liquid.

Moreover, so as to permit immediate commencement of priming and backpriming operations after the package has been opened and the infusion set has been removed therefrom, an infusion set in accordance with the present invention may be provided in presterilized form. There is no particular limitation with regard to the method for sterilization of the infusion set, it being possible to use methods such as are ordinarily employed as methods for sterilization of infusion sets and/or medical equipment; for example, methods which include ethylene oxide gas sterilization, γ irradiation sterilization, e-beam sterilization, radiation sterilization, ultraviolet irradiation sterilization, hydrogen peroxide sterilization, and ethanol sterilization may be employed. In addition, as said sterilization method, it is preferred based on considerations which include ease of manufacturing and cost reduction that ethylene oxide gas sterilization, e-beam sterilization, and/or γ irradiation sterilization be employed. It is preferred that e-beam sterilization be carried out to such a degree as will not cause degradation of the infusion set, and it is preferred that the irradiative energy during γ irradiation sterilization be within a range that is up to on the order of 5 kGy to 30 kGy so as to cause sterilization to be carried out to such a degree as will not cause degradation of the infusion set.

Pretreatment Method Comprising Priming and Backpriming at Infusion Set Employing Spike Cap in Accordance with the Present Invention At an infusion set employing a spike cap in accordance with the present invention, prior to administering an infusion to a patient by intravenous drip infusion, preprocessing operations comprising priming and backpriming are carried out in advance so as to remove air from the interior of the infusion set and cause it to be filled with physiological saline solution or other such solution.

A package, sealed within which there is an infusion set employing spike cap(s) in accordance with the present invention, is opened, and the infusion set is investigated to make sure that spike cap(s) 1 and cap(s) 10 for connector(s) for connection with intravenous drip needle(s) provided with lid(s) are definitively installed thereon, and to make sure that lid(s) 1*d*, 10*d* of the respective caps are open. Furthermore, investigation is carried out to make sure that all shutoff clamp(s) 3 are in their open state. Investigation is carried out to make sure that lever(s) 7*d* of three-way stopcock(s) at which infusion tubing connected to spike(s) is/are connected at secondary tubing branch(es) is/are in position(s) permitting flow to/from all three branches. Furthermore, investigation is carried out to make sure that roller clamp(s) 9 are in their open state (FIG. 5).

Next, infusion container 5 having sealed therewithin physiological saline solution 6 for use during priming and backpriming is suspended from an IV stand. In addition, the cap installed on the spike 2 disposed at the upstream-most location in the infusion set of the present invention is removed, the seal of said infusion container 5 suspended from the IV stand is pierced with spike 2 disposed at the upstream-most location in the infusion set, and priming and backpriming operations are initiated (FIG. 5). Where the IV stand is equipped with a stay rod for securing drip chamber 8 or other such securing hardware, this may be used to secure the foregoing. Note that while securing need not be carried out during preprocessing comprising priming and backpriming, it is preferred that securing hardware be used to secure drip chamber 8 when initiating intravenous drip infusion, to prevent the entire weight of the infusion set from being borne by intravenous drip needle(s) and connector(s) for connection with intravenous drip needle(s), so that region(s) at which intravenous drip needle(s) are inserted are not placed under stress.

Physiological saline solution 6 flows into infusion tubing 4 from infusion container 5 placed on spike 2 disposed at the upstream-most location, and priming operations commence. As physiological saline solution 6 displaces air within infusion tubing 4, it flows from primary tubing upstream branch connector 7*a* of the three-way stopcock 7 which is disposed downstream therefrom into three-way stopcock 7. Because lever 7*d* of said three-way stopcock 7 is positioned so as to permit flow to/from all three branches, as physiological saline solution 6 flowing thereinto displaces air within three-way stopcock 7, it further flows into primary tubing downstream branch connector 7*b* and secondary tubing branch connector 7*c* of the three-way stopcock.

Furthermore, physiological saline solution 6 that has flowed into secondary tubing branch connector 7*c* of the aforesaid three-way stopcock, being physiological saline solution for carrying out backpriming, as it displaces air within infusion tubing 4 which is further connected thereto, flows into spike 2 which is connected at the far side thereof. As it flows thereinto, physiological saline solution 6 displaces the air at the interior of spike 2, and as it does so, it flows from spike 2 into the interior of spike cap 1 of the present invention, which is installed on said spike. In addition, air that had been present in the region from the periphery at the tip of the spike to the interior sidewall of the cap at hydrophobic filter 1*b* is displaced therefrom by physiological saline solution 6 which flows thereinto, passes through hydrophobic filter 1*b*, and is discharged to the exterior by way of cap opening 1*c*, as a result of which that portion becomes filled with physiological saline solution 6. Here, hydrophobic filter 1*b* does not permit passage therethrough of physiological saline solution 6. Furthermore, air remains in the portion toward the base from the tip of spike 2 from which physiological saline solution 6 flows at the cap interior ((c) at FIG. 1).

On the other hand, physiological saline solution 6 which has flowed into the interior of primary tubing downstream branch connector 7*b* at the aforesaid three-way stopcock 7 further flows into infusion tubing 4 which is connected thereto and displaces the air therewithin to a location downstream therefrom.

In the event that three-way stopcock(s) 7 is/are further connected at the far end of said infusion tubing 4, physiological saline solution 6 that has flowed thereinto, being physiological saline solution 6 for carrying out backpriming, further flows in order, in the same fashion as has been described above, into secondary tubing branch connector(s) 7*c* of three-way stopcock(s), interior(s) of infusion tubing 4, interior(s) of spike(s) 2, and interior(s) of spike cap(s) 1 of the present invention. In addition, physiological saline solution 6 which flows thereinto causes air present in the region from the periphery at the tip of the spike into which physiological saline solution 6 flows to the interior sidewall of the cap at hydrophobic filter 1 to pass through hydrophobic filter 1*b* and to be displaced to the exterior by way of cap opening 1*c*, as a result of which that portion becomes filled with physiological saline solution. Here, hydrophobic filter 1b does not permit passage therethrough of physiological saline solution 6. Furthermore, air remains in the portion toward the base from the tip of spike 2 from which physiological saline solution 6 flows at the interior of cap 1.

In addition, physiological saline solution 6 which has flowed into the interior of primary tubing downstream branch connector 7b at the aforesaid three-way stopcock 7 displaces air from within infusion tubing 4 further connected thereto to a location downstream therefrom, and in so doing causes it to flow into drip chamber 8 which is connected at the far end thereof. Physiological saline solution 6 which flows thereinto displaces air from within infusion tubing 4 further connected thereto to a location downstream therefrom, and as it does so it flows therealong to flow into a connector for connection with an intravenous drip needle.

After flowing into the connector for connection with the intravenous drip needle, physiological saline solution 6 displaces the air therewithin to a location downstream therefrom, and as it does so it flows from the tip of the connector for connection with the intravenous drip needle to the interior of the cap 10 for the connector for connection with the intravenous drip needle. In addition, physiological saline solution 6 which has flowed thereinto causes air that had been present in the region peripheral thereto to further pass through hydrophobic filter 10b and to be displaced to the exterior by way of cap opening 10c, as a result of which the region peripheral thereto becomes filled with physiological saline solution 6. Here, hydrophobic filter 10b does not permit passage therethrough of physiological saline solution 6. Furthermore, air remains in the portion toward the base from the tip of the connector for connection with the intravenous drip needle from which physiological saline solution 6 flows at the interior of cap 7.

Figure 6:
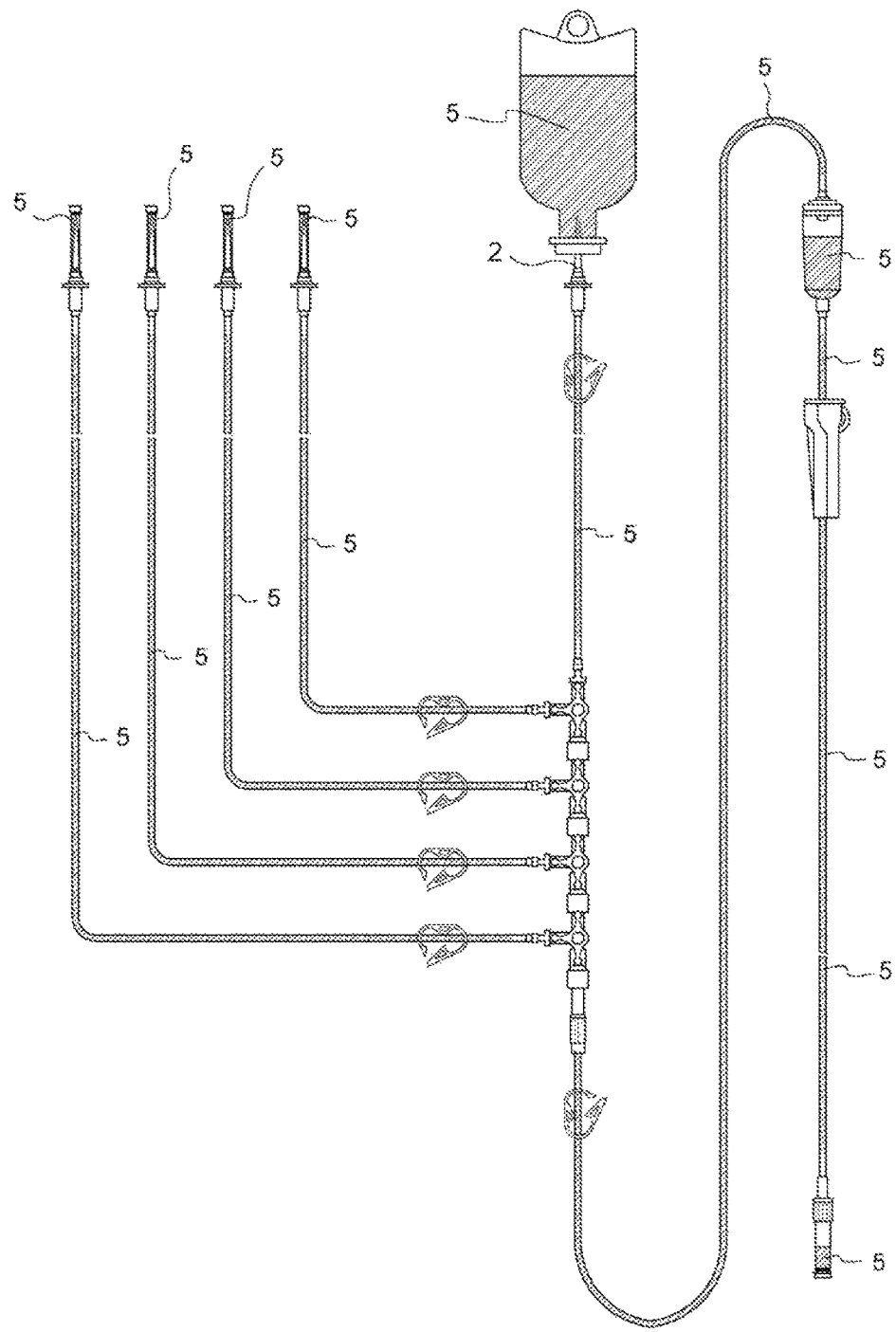
FIG. 6 Drawing for explaining a situation that may exist when caps 1 and lids 1d, 10d are closed following completion of preprocessing comprising priming and backpriming in the context of an infusion set employing spike caps 1 in accordance with the present invention.

In this way, at an infusion set employing a spike cap in accordance with the present invention, preprocessing comprising priming and backpriming are completed not only at primary tubing branch(es) but also at secondary tubing branch(es) by causing air within said infusion set to be quickly discharged therefrom and simultaneously causing said infusion set to be filled with physiological saline solution as a result of only a single operation in which "a spike 2 disposed at an upstream-most location in said infusion set is inserted in an infusion container 5 which has sealed therewithin physiological saline solution 6 for use during priming and backpriming" (FIG. 6). Furthermore, even where there are a plurality of linked three-way stopcocks with a plurality of sets of secondary tubing being provided thereat, at an infusion set in accordance with the present invention, preprocessing comprising priming and backpriming are completed in the same manner as described above not only at the primary tubing branch but also at the plurality of secondary tubing branches by causing air within said infusion set to be quickly discharged therefrom and simultaneously causing the interiors to be filled with physiological saline solution as a result of only the aforesaid single operation (FIG. 6). In addition, regardless of which of the foregoing situations applies, because hydrophobic filter(s) 1b, 10b is/are present at cap(s) 10 for connector(s) for connection with intravenous drip needle(s) and spike cap(s) 1, there will be no occurrence of leakage of liquid even if lid(s) is/are open.

During the aforesaid preprocessing operations comprising priming and backpriming, because hydrophobic filter(s) 1b, 10b is/are present, there will be absolutely no discharge of unwanted liquid, and there will be no occurrence of damage to equipment and/or contamination of the hospital room interior. Moreover, because the amount of the physiological saline solution sealed within the infusion container connected to the spike at the upstream-most location that is used can be kept to a minimum, such that an adequate remaining amount is retained therewithin, this permits effective use thereof, as there may be no need to replace the infusion container at the time of medical treatment that may take place thereafter. Furthermore, because an infusion set employing spike cap(s) in accordance with the present invention is assembled in advance in the form of a single integral unit, there being no occurrence of unintentional leakage of liquid during preprocessing operations comprising priming and backpriming, there will be no occurrence of damage to equipment and/or contamination of the hospital room interior.

After completion of preprocessing comprising priming and backpriming, in the event that medical treatment with intravenous drip infusion is to be initiated, lid(s) 1d, 10d at cap(s) for connector(s) for connection with intravenous drip needle(s) and spike cap(s) are first closed (FIG. 6). In addition, shutoff clamp(s) 3 disposed at respective set(s) of infusion tubing 4 is/are pinched together, and roller clamp(s) 9 is/are moved to their closed position(s), to close off the respective set(s) of infusion tubing 4. Furthermore, lever(s) 7d at three-way stopcock(s) 7 is/are moved to position(s) corresponding to the intravenous drip infusion(s) to be initiated.

Spike cap(s) 1 in accordance with the present invention is/are removed from where it/they is/are installed on spike(s) 2 to which therapeutic agent(s) is/are connected (also see (e) at FIG. 1). Furthermore, cap(s) 10 is/are also removed from where it/they is/are installed on connector(s) for connection with intravenous drip needle(s). In addition, said spike 2 is made to pierce infusion container 5 within which a therapeutic solution is sealed, and a connector for connection with an intravenous drip needle is connected to an intravenous drip needle. Notwithstanding that the foregoing operations are carried out, because tubing at the infusion set has been placed in its closed state, there is no leakage of physiological saline solution 6 used for priming and backpriming from spike(s) 2 or connector(s) for connection with intravenous drip needle(s) removed therefrom, and there is no occurrence of damage to equipment and/or contamination of the hospital room interior. Furthermore, because lid(s) is/are shut at the aforesaid cap(s) 1, 10, air does not flow thereinto and there is no air that again passes therethrough from hydrophobic filter(s) 1b, 10b, and moreover, surface tension due to the physiological saline solution and atmospheric pressure from opening(s) 1c, 10c at the cap(s) act in such fashion that physiological saline solution 6 at region(s) peripheral to hydrophobic filter(s) at the interior does not spill out from insertion port(s) 1a, 10a at cap(s), and there is no occurrence of damage to equipment and/or contamination of the hospital room interior (see also (e) at FIG. 1).

Furthermore, in accordance with another aspect of the present invention, spike cap 1, to prevent untimely detachment during preprocessing operations comprising priming and backpriming, has clip(s) 1f equipped with catch(es) 1e for engagement with flange(s) 2a provided on spike 2. During use, catch 1e of clip 1f which is present on spike cap 1 in accordance with the present invention is secured by causing it to engage with flange 2a provided on spike 2 ((a) at FIG. 3, (b) at FIG. 3, (c) at FIG. 3).

Moreover, in accordance with another aspect of the present invention, spike cap 1 is equipped with hook(s) for anchoring said cap to infusion tubing. Where the cap has C-shaped hook 1g and/or U-shaped hook 1i, infusion tubing 4 is secured by causing it to be squeezed at the desired location(s) within the C-shaped and/or U-shaped portion(s) of said hook(s) (see also (a) at FIG. 2, (b) at FIG. 2, and (d) at FIG. 2). Where O-shaped hook(s) 1h is/are employed, because infusion tubing is made to pass through the O-shaped hole(s) of the hook(s) at the time of manufacturing, securing is accomplished by moving the hook(s) to the desired location(s) (see also (b) at FIG. 2). Spike cap(s) 1 in accordance with the present invention which is/are equipped with hook(s) is/are secured to infusion tubing 4 at primary tubing branch(es). Where there are a plurality of sets of secondary tubing due to the fact that there are a plurality of linked three-way stopcocks 7, spike caps 1 in accordance with the present invention which are equipped with respective hooks might be secured to infusion tubing 4 at primary tubing branches. Moreover, infusion tubing may optionally be organized by bundling tubing together with paper tape or the like. By securing these as described above, center(s) of gravity of infusion line(s) connected to secondary tubing branch(es) and spike cap(s) 1 in accordance with the present invention is/are made to shift toward primary tubing branch(es), increasing stability of IV stand(s) during preprocessing comprising priming and backpriming, during administration of infusion(s), and so forth.

By using spike cap(s) 1 equipped with hook(s) as described above, because cap(s) may be left anchored to infusion tubing, it is possible to become free of the risks of damage to equipment and contamination of the hospital room interior that can occur due to splattering of physiological saline solution remaining in cap interior(s) when cap(s) that have been removed slip from the fingers or is/are otherwise allowed to fall following backpriming.

Furthermore, where there are a plurality of sets of secondary tubing due to the fact that there are a plurality of linked three-way stopcocks 7, it is necessary that adequate attention be paid so as not to confuse the order of use of secondary tubing. In particular, where an anticancer agent or other such drug contraindicated for mixture with different drug(s) is being used, it will be necessary to first use the secondary tubing set connected to the downstream three-way stopcock and to thereafter use the secondary tubing set(s) connected to three-way stopcock(s) upstream therefrom in sequence. Here, spike caps 1 in accordance with the present invention which are equipped with respective hooks are anchored to infusion tubing 4 at primary tubing branches in stacked fashion in order of use starting from the top (FIG. 4). By so doing, because the procedure for use of secondary tubing set(s) at the infusion set will have been made consistent, it will be possible, without misidentification of sequence, to definitively select the secondary tubing branch tubing that should be used; and because standardization of operational procedures will have been made extremely simple, it will be possible to become free of the risk of occurrence of human error.

Working Examples

Indicated below are working examples of manufacture and use of infusion sets in accordance with the present invention. The present invention is not to be limited in any way by these descriptions.

Members for constructing an infusion set in accordance with the present invention were prepared in the form of a spike cap characterized in that arranged thereat was an opening configured so as to not allow passage therethrough of solid or liquid but so as to allow passage therethrough of gas at the interior of the cap, a hydrophobic filter being arranged at a location inward from where the tip of the spike was inserted at the interior of the cap by way of an insertion port for the spike, and a lid at the exterior of said opening for closing said opening; a spike; a three-way stopcock; a male connector; a drip chamber; a roller clamp; a connector for connection with an intravenous drip needle; infusion tubing; a shutoff clamp for pressing on and opening and/or closing flow path(s) within infusion tubing; and a cap for a connector for connection with an intravenous drip needle, arranged at which there was an opening configured so as to not allow passage therethrough of solid or liquid but so as to allow passage therethrough of gas at the interior of the cap, a hydrophobic filter being arranged at a location inward from where the tip of the connector for connection with the intravenous drip needle was inserted at the interior of the cap by way of an insertion port for the connector for connection with the intravenous drip needle, and a lid at the exterior of said opening for closing said opening.

The foregoing members were connected to form of a single integral unit as described at the section entitled Configuration and Constitution of Infusion Set of Present Invention and the section entitled Manufacturing Operations. In addition, lids of caps were opened, all shutoff clamps were placed in their open states, levers of three-way stopcocks were moved to positions permitting flow to/from all three branches, and roller clamp 3 was placed in its open state, to manufacture an infusion set in accordance with the present invention.

As shown in FIG. 5, an infusion set equipped with four sets of secondary tubing was manufactured as Working Example 1.

As Working Example 2, an infusion set in which, instead of the spike caps employed at Working Example 1, members were employed which were such that clips equipped with catches for flanges of spikes were further provided on said caps, but which in other respects was identical to Working Example 1, was manufactured.

As Working Example 3, an infusion set in which, instead of the spike caps employed at Working Example 1, members were employed which were such that hooks of C-shaped configuration for anchoring to infusion tubing were provided on said caps, the caps being anchored to infusion tubing as shown in FIG. 4, but which in other respects was identical to Working Example 1, was manufactured.

As Comparative Example 1, an infusion set in which, instead of the caps having lids and hydrophobic filters employed at Working Example 1, caps were employed that differed only with respect to the fact that they were not provided with lids for closing openings, but which in other respects was identical to Working Example 1, was manufactured.

An infusion container having sealed therewithin physiological saline solution was suspended from an IV stand, the spike disposed at the upstream-most location in the infusion set was made to pierce the rubber seal of said infusion container, and preprocessing operations comprising priming and backpriming were initiated. Testing was respectively carried out using the respective infusion sets at Working Example 1 through Working Example 3 and at Comparative Example 1.

As a result, regardless of which infusion set was used, it was observed that preprocessing comprising priming and backpriming of the infusion set could be completed as a result of only a single operation in which a spike was made to pierce the seal of an infusion container, the interior of the infusion set being filled with physiological saline solution, with only the air at the interior of the infusion set that was displaced by said physiological saline solution being exhausted by way of hydrophobic filters respectively provided at caps. There was no leakage of physiological saline solution from any of the connections between/among the various members. At Working Example 2, because clips equipped with catches for flanges of spikes were provided on caps, the caps could be more securely installed on spikes than was the case elsewhere.

Next, following completion of preprocessing operations comprising priming and backpriming, the lids for closing the openings at the caps at the foregoing respective infusion sets were closed (Working Examples 1 through 3). Note that there were no lids on the caps at Comparative Example 1. In addition, shutoff clamps 3 disposed at the respective sets of infusion tubing were pinched together, and roller clamp 9 was moved to its closed position, to close off the respective sets of infusion tubing. Furthermore, levers at three-way stopcocks were moved to positions corresponding to the intravenous drip infusion to be initiated.

Caps at Working Examples 1 through 3 and Comparative Example 1 were removed from spikes and connectors for connection with intravenous drip needles.

As a result, because the lids were closed at the caps at Working Examples 1 through 3, air did not pass through the hydrophobic filters to reenter the cap interiors, and as a result of the action of surface tension due to the physiological saline solution and atmospheric pressure from the openings at the caps, physiological saline solution at regions peripheral to the hydrophobic filters at the interior did not spill out from the insertion ports at the caps. At Working Example 3, because caps were anchored to infusion tubing by C-shaped hooks, there was no concern that the caps would come off at the time that the spikes and the connectors for connection with intravenous drip needles were being detached. Furthermore, physiological saline solution did not drip out of the spikes or the connectors for connection with intravenous drip needles after they were detached.

However, at Comparative Example 1, which did not have lids, following removal of the caps from the spikes and the connectors for connection with intravenous drip needles, air did pass through the hydrophobic filters provided at those caps to reenter the cap interiors, and physiological saline solution that had remained at the cap interiors leaked out via the insertion ports for the spikes and connectors for connection with intravenous drip needles at the caps and spilled out to the exterior.

INDUSTRIAL UTILITY

In accordance with the means of the present invention, preprocessing operations comprising priming and backpriming can be carried out as a result of only a single operation in which a spike is made to pierce the seal of an infusion container containing physiological saline solution, and, there being no unintentional leakage of liquid while operations are being carried out or after operations have been carried out, it is possible to drastically reduce the risk of occurrence of damage to equipment and contamination of the hospital room interior, and the physiological saline solution can also be utilized in effective fashion during any medical treatment that may take place thereafter. Moreover, in accordance with the means of the present invention, it is possible to provide a novel infusion set in which, by using hook(s) provided at spike cap(s) to anchor spike(s) to infusion tubing, it is possible where a plurality of spikes are provided to cause the order of use thereof to be made clear, making it possible to prevent occurrence of accidents occurring due to human error such as confusing which infusion is which among multiple pieces of infusion tubing and/or error in the order in which infusions are to be administered, and that moreover makes it possible to easily establish standard procedures for use.

EXPLANATION OF REFERENCE NUMERALS

1 Spike cap
1a Insertion port for spike
1b Hydrophobic filter
1c Opening
1d Lid
1e Catch
1f Clip
1g C-shaped hook
1h O-shaped hook
1i U-shaped hook
2 Spike
2a Flange
3 Shutoff clamp
4 Infusion tubing
4a Infusion tubing (sectional view)
5 Infusion container
6 Physiological saline solution
7 Three-way stopcock
7a Primary tubing upstream branch connector
7b Primary tubing downstream branch connector
7c Secondary tubing branch connector
7d Lever
8 Drip chamber
9 Roller clamp
10 Cap for connector for connection with intravenous drip needle
10a Insertion port for connector for connection with intravenous drip needle
10b Hydrophobic filter
10c Opening
10d Lid

The invention claimed is:
1. A spike cap, comprising:
an opening for not allowing passage of solids or liquids but for allowing passage of gas from an interior of the cap,
a hydrophobic filter arranged at a location inward from an insertion port where a tip of a spike is inserted into the interior of the cap, said hydrophobic filter not allowing passage of solids or liquids to said opening but allowing passage of gas to said opening, whereby air passes through the hydrophobic filter and is discharged through the opening, and
a lid for closing said opening at an exterior of said opening.
2. The spike cap according to claim 1, wherein arranged at an exterior of the insertion port for the spike is a lid for closing said insertion port.
3. The spike cap according to claim 1, wherein the spike cap has a clip equipped with a catch for a flange disposed on the spike.
4. The spike cap according to claim 1, wherein the spike cap has a hook for anchoring to infusion tubing.
5. The spike cap according to claim 4, wherein the hook has a C-shaped configuration, an O-shaped configuration, or a U-shaped configuration.

6. The spike cap according to claim 4, wherein the hook is arranged on said cap such as to cause the insertion port for the spike to be inclined upward or such as to cause said cap to be horizontal when the aforesaid cap is anchored to infusion tubing connected to the spike which is provided at an upstream-most location of a primary tubing branch.

7. An infusion set wherein the spike cap according to claim 1 is installed on a spike connected to an end of infusion tubing that is linked to a secondary tubing branch connector at a three-way stopcock or splitter at the infusion set, and installed at a connector for connection with an intravenous drip needle provided at a downstream-most location of a primary tubing branch in said infusion set is a cap which is for a connector for connection with an intravenous drip needle and arranged at which there is an opening configured to not allow passage there-through of solid or liquid but so as to allow passage there-through of gas at the interior of the cap, a hydrophobic filter being arranged at a location inward from where the tip of the connector for connection with an intravenous drip needle is inserted at the interior of the cap by way of the insertion port for the connector for connection with an intravenous drip needle, and a lid for closing said opening at the exterior of said opening.

8. A preprocessing method comprising priming and back-priming of the infusion set according to claim 7, the preprocessing method comprising:
    priming and back-priming of said infusion set including that as a result of a single operation in which the spike disposed at an upstream-most location of the primary tubing branch in the infusion set, at which the lids arranged at the opening for the cap for the connector for connection with the intravenous drip needle and the spike cap, infusion set shutoff clamps, levers of three-way stopcocks, and a roller clamp are all placed in their open states, is made to pierce a rubber seal of an infusion container having physiological saline solution sealed there-within, the physiological saline solution is made to enter an internal cavity of the infusion set, causing air at the interior of the infusion set to be displaced and to be exhausted by way of the hydrophobic filters arranged at the spike cap and cap for the connector for connection with the intravenous drip needle, and causing the internal cavity to be filled with the physiological saline solution, as a result of which priming and back-priming are completed.

* * * * *